(12) United States Patent
Marecki et al.

(10) Patent No.: US 12,349,906 B2
(45) Date of Patent: *Jul. 8, 2025

(54) MULTIDIRECTIONAL APPARATUS

(71) Applicant: Lexington Medical, Inc., Bedford, MA (US)

(72) Inventors: Andrew Marecki, Wilbraham, MA (US); David T. Moy, Jr., Wellesley, MA (US); Leon Amariglio, Lexington, MA (US)

(73) Assignee: Lexington Medical, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/543,682

(22) Filed: Dec. 18, 2023

(65) Prior Publication Data

US 2024/0115260 A1 Apr. 11, 2024

Related U.S. Application Data

(63) Continuation of application No. 17/689,549, filed on Mar. 8, 2022, now Pat. No. 11,844,523, which is a
(Continued)

(51) Int. Cl.
*A61B 17/072* (2006.01)
*A61B 17/00* (2006.01)
*A61B 34/30* (2016.01)

(52) U.S. Cl.
CPC ............... *A61B 17/07207* (2013.01); *A61B 2017/00314* (2013.01); *A61B 2017/00327* (2013.01);
(Continued)

(58) Field of Classification Search
CPC ................................. A61B 17/07207
See application file for complete search history.

(56) References Cited

U.S. PATENT DOCUMENTS 3,142,187 A 7/1964 Hugh et al.
3,517,570 A 6/1970 Kolb
(Continued)

FOREIGN PATENT DOCUMENTS

CN 1985768 B 9/2011
CN 101194853 B 7/2012
(Continued)

OTHER PUBLICATIONS

Final Office Action received in U.S. Appl. No. 15/631,429 dated Jan. 10, 2020, 17 pages.
(Continued)

*Primary Examiner* — Nathaniel C Chukwurah
(74) *Attorney, Agent, or Firm* — Perkins Coie LLP

(57) ABSTRACT

The present disclosure is directed to a multidirectional apparatus that can be attached to a stapler reload apparatus. The multidirectional apparatus can include at least two articulation elements each comprising a cylindrical proximal end, a hemispherical distal end, a central lumen, a wall surrounding the central lumen, and a first pull wire lumen within the wall surrounding the central lumen, wherein the hemispherical distal end of a first articulation element of the at least two articulation elements is nested in the cylindrical proximal end of a second articulation element of the at least two articulation elements and a first pull wire positioned within the first pull wire lumen, and wherein tension applied to the first pull wire causes the second articulation element to move away from a longitudinal axis of the at least two articulation elements in a direction of the first pull wire which is experiencing the tension.

20 Claims, 13 Drawing Sheets

Related U.S. Application Data continuation of application No. 16/743,317, filed on Jan. 15, 2020, now Pat. No. 11,298,131.

(52) U.S. Cl.
CPC ............ *A61B 2017/0053* (2013.01); *A61B 2017/00734* (2013.01); *A61B 2017/00867* (2013.01); *A61B 2017/07257* (2013.01); *A61B 34/30* (2016.02)

(56) References Cited

U.S. PATENT DOCUMENTS

| | | |
|---|---|---|
| 3,919,506 A | 11/1975 | Kellogg |
| RE28,932 E | 8/1976 | Noiles et al. |
| 4,175,220 A | 11/1979 | Johnston et al. |
| 4,737,608 A | 4/1988 | Jones |
| 4,754,909 A | 7/1988 | Barker et al. |
| 4,884,478 A | 12/1989 | Lieser |
| 4,978,049 A | 12/1990 | Green |
| 5,300,081 A | 4/1994 | Young et al. |
| 5,322,161 A | 6/1994 | Shichman et al. |
| 5,325,987 A | 7/1994 | Alpern et al. |
| 5,326,013 A | 7/1994 | Green et al. |
| RE34,680 E | 8/1994 | Lieser |
| 5,379,895 A | 1/1995 | Foslien |
| 5,453,094 A | 9/1995 | Metcalf et al. |
| 5,474,223 A | 12/1995 | Viola et al. |
| 5,489,058 A | 2/1996 | Plyley et al. |
| 5,489,292 A | 2/1996 | Tovey et al. |
| 5,507,426 A | 4/1996 | Young et al. |
| 5,522,534 A | 6/1996 | Viola et al. |
| 5,535,935 A | 7/1996 | Vidal et al. |
| 5,586,711 A | 12/1996 | Plyley et al. |
| 5,588,579 A | 12/1996 | Schnut et al. |
| 5,601,224 A | 2/1997 | Bishop et al. |
| 5,632,432 A * | 5/1997 | Schulze ............ A61B 17/07207 227/176.1 |
| 5,651,491 A | 7/1997 | Heaton et al. |
| 5,702,408 A | 12/1997 | Wales et al. |
| 5,713,505 A | 2/1998 | Huitema |
| 5,743,350 A | 4/1998 | Yamawaki et al. |
| 5,752,590 A | 5/1998 | Lin |
| 5,758,814 A | 6/1998 | Gallagher et al. |
| 5,762,256 A | 6/1998 | Mastri et al. |
| 5,799,857 A | 9/1998 | Robertson et al. |
| 5,823,066 A | 10/1998 | Huitema et al. |
| 5,836,503 A | 11/1998 | Ehrenfels et al. |
| 5,862,715 A | 1/1999 | Lemire |
| 5,865,361 A | 2/1999 | Milliman et al. |
| 5,901,895 A | 5/1999 | Heaton et al. |
| 6,109,500 A | 8/2000 | Alli et al. |
| 6,281,453 B1 | 8/2001 | Uleski |
| 6,302,798 B1 | 10/2001 | Nakaguro et al. |
| 6,945,444 B2 | 9/2005 | Gresham et al. |
| 6,957,758 B2 | 10/2005 | Aranyi |
| 6,981,628 B2 | 1/2006 | Wales |
| 7,044,352 B2 | 5/2006 | Shelton et al. |
| 7,044,353 B2 | 5/2006 | Mastri et al. |
| 7,097,089 B2 | 8/2006 | Marczyk |
| 7,143,923 B2 | 12/2006 | Shelton et al. |
| 7,143,924 B2 | 12/2006 | Scirica et al. |
| 7,168,604 B2 | 1/2007 | Milliman et al. |
| 7,225,963 B2 | 6/2007 | Scirica |
| 7,234,624 B2 | 6/2007 | Gresham et al. |
| 7,303,106 B2 | 12/2007 | Milliman et al. |
| 7,325,713 B2 | 2/2008 | Aranyi |
| 7,364,060 B2 | 4/2008 | Milliman |
| 7,380,695 B2 | 6/2008 | Doll et al. |
| 7,380,696 B2 | 6/2008 | Shelton et al. |
| 7,398,907 B2 | 7/2008 | Racenet et al. |
| 7,404,508 B2 | 7/2008 | Smith et al. |
| 7,422,136 B1 | 9/2008 | Marczyk |
| 7,431,188 B1 | 10/2008 | Marczyk |
| 7,455,208 B2 | 11/2008 | Wales et al. |
| 7,490,749 B2 | 2/2009 | Schall et al. |
| 7,494,038 B2 | 2/2009 | Milliman |
| 7,516,877 B2 | 4/2009 | Aranyi |
| 7,546,940 B2 | 6/2009 | Milliman et al. |
| 7,611,038 B2 | 11/2009 | Racenet et al. |
| 7,624,902 B2 | 12/2009 | Marczyk et al. |
| 7,657,974 B2 | 2/2010 | Huang |
| 7,694,865 B2 | 4/2010 | Scirica |
| 7,703,653 B2 | 4/2010 | Shah et al. |
| 7,780,055 B2 | 8/2010 | Scirica et al. |
| 7,802,712 B2 | 9/2010 | Milliman et al. |
| 7,824,426 B2 | 11/2010 | Racenet et al. |
| 7,832,408 B2 | 11/2010 | Shelton et al. |
| 7,837,079 B2 | 11/2010 | Holsten et al. |
| 7,845,535 B2 | 12/2010 | Scircia |
| 7,857,187 B2 | 12/2010 | Milliman |
| 7,870,810 B2 | 1/2011 | Da et al. |
| 7,900,805 B2 | 3/2011 | Shelton et al. |
| 7,926,692 B2 | 4/2011 | Racenet et al. |
| 7,963,431 B2 | 6/2011 | Scirica |
| 7,967,178 B2 | 6/2011 | Scirica et al. |
| 7,967,180 B2 | 6/2011 | Scirica |
| 7,988,028 B2 | 8/2011 | Farascioni et al. |
| 8,020,743 B2 | 9/2011 | Shelton |
| 8,056,789 B1 | 11/2011 | White et al. |
| 8,061,576 B2 | 11/2011 | Cappola |
| 8,070,036 B1 | 12/2011 | Knodel |
| 8,123,101 B2 | 2/2012 | Racenet et al. |
| 8,136,712 B2 | 3/2012 | Zingman |
| 8,141,763 B2 | 3/2012 | Milliman |
| 8,157,148 B2 | 4/2012 | Scirica |
| 8,235,274 B2 | 8/2012 | Cappola |
| 8,292,157 B2 | 10/2012 | Smith et al. |
| 8,292,905 B2 | 10/2012 | Taylor et al. |
| 8,328,822 B2 | 12/2012 | Huitema et al. |
| 8,336,751 B2 | 12/2012 | Scirica |
| 8,336,754 B2 | 12/2012 | Cappola et al. |
| 8,342,378 B2 | 1/2013 | Marczyk et al. |
| 8,360,296 B2 | 1/2013 | Zingman |
| 8,413,868 B2 | 4/2013 | Cappola |
| 8,424,736 B2 | 4/2013 | Scirica et al. |
| 8,573,460 B2 | 11/2013 | Cappola |
| 8,573,463 B2 | 11/2013 | Scirica et al. |
| 8,584,919 B2 | 11/2013 | Hueil et al. |
| 8,608,043 B2 | 12/2013 | Scirica |
| 8,622,894 B2 | 1/2014 | Banik et al. |
| 8,632,535 B2 | 1/2014 | Shelton et al. |
| 8,684,247 B2 | 4/2014 | Scirica et al. |
| 8,684,249 B2 | 4/2014 | Racenet et al. |
| 8,695,865 B2 | 4/2014 | Smith et al. |
| 8,888,814 B2 | 11/2014 | Cappola |
| 8,910,847 B2 | 12/2014 | Nalagatla et al. |
| 9,060,770 B2 | 6/2015 | Shelton et al. |
| 9,072,523 B2 | 7/2015 | Houser et al. |
| 9,089,338 B2 | 7/2015 | Smith et al. |
| 9,204,876 B2 | 12/2015 | Cappola et al. |
| 9,241,715 B2 | 1/2016 | Kasvikis et al. |
| 9,268,356 B2 | 2/2016 | Burleson |
| 9,282,966 B2 | 3/2016 | Shelton et al. |
| 9,346,223 B2 | 5/2016 | Payne |
| 9,364,218 B2 | 6/2016 | Scirica |
| 9,393,016 B2 | 7/2016 | Scirica et al. |
| 9,463,022 B2 | 10/2016 | Swayze et al. |
| 9,539,006 B2 | 1/2017 | Collings et al. |
| 9,655,617 B2 | 5/2017 | Cappola |
| 9,679,716 B2 | 6/2017 | Faurie et al. |
| 9,844,378 B2 | 12/2017 | Casasanta et al. |
| 9,855,040 B2 | 1/2018 | Kostrzewski |
| 9,861,358 B2 | 1/2018 | Marczyk et al. |
| 9,931,739 B2 | 4/2018 | Nelson et al. |
| 10,039,546 B2 | 8/2018 | Williams et al. |
| 10,383,634 B2 | 8/2019 | Shelton et al. |
| 10,413,291 B2 | 9/2019 | Worthington et al. |
| 10,668,600 B1 | 6/2020 | Ye et al. |
| 10,849,621 B2 | 12/2020 | Whitfield et al. |
| 10,905,422 B2 | 2/2021 | Bakos et al. |
| 10,912,560 B2 | 2/2021 | Marecki et al. |
| 11,116,501 B1 | 9/2021 | Marecki |
| 11,185,326 B2 | 11/2021 | Kostrzewski et al. |

(56) References Cited

U.S. PATENT DOCUMENTS

| | | |
|---|---|---|
| 11,298,131 B2 | 4/2022 | Marecki et al. |
| 11,376,003 B2 | 7/2022 | Somekh et al. |
| 11,510,668 B2 | 11/2022 | Racenet et al. |
| 11,617,582 B2 | 4/2023 | Marecki et al. |
| 11,771,424 B2 | 10/2023 | Marecki |
| 11,844,523 B2 | 12/2023 | Marecki et al. |
| 2001/0030219 A1 | 10/2001 | Green et al. |
| 2004/0232199 A1 | 11/2004 | Shelton et al. |
| 2005/0006429 A1 | 1/2005 | Wales et al. |
| 2005/0116009 A1 | 6/2005 | Milliman |
| 2005/0139635 A1 | 6/2005 | Wukusick et al. |
| 2006/0079912 A1 | 4/2006 | Whitfield et al. |
| 2006/0111210 A1 | 5/2006 | Hinman |
| 2007/0125826 A1 | 6/2007 | Shelton |
| 2007/0262116 A1 | 11/2007 | Hueil et al. |
| 2008/0017693 A1 | 1/2008 | Mastri et al. |
| 2008/0083810 A1 | 4/2008 | Marczyk |
| 2008/0179374 A1 | 7/2008 | Beardsley et al. |
| 2008/0179375 A1 | 7/2008 | Scirica |
| 2008/0308607 A1 | 12/2008 | Timm et al. |
| 2009/0062614 A1 | 3/2009 | Adzich et al. |
| 2009/0145947 A1 | 6/2009 | Scirica et al. |
| 2009/0206137 A1 | 8/2009 | Hall et al. |
| 2009/0272614 A1 | 11/2009 | Watarai |
| 2010/0001036 A1 | 1/2010 | Marczyk et al. |
| 2010/0193568 A1 | 8/2010 | Scheib et al. |
| 2010/0264193 A1 | 10/2010 | Huang et al. |
| 2011/0062211 A1 | 3/2011 | Ross et al. |
| 2011/0253765 A1 | 10/2011 | Nicholas et al. |
| 2011/0290854 A1 | 12/2011 | Timm et al. |
| 2011/0295242 A1 | 12/2011 | Spivey et al. |
| 2012/0053406 A1 | 3/2012 | Conlon et al. |
| 2012/0111591 A1 | 5/2012 | Shelton et al. |
| 2012/0138659 A1 | 6/2012 | Marczyk et al. |
| 2012/0168484 A1 | 7/2012 | Scirica et al. |
| 2012/0271284 A1 | 10/2012 | Cappola |
| 2012/0286019 A1 | 11/2012 | Hueil et al. |
| 2013/0092719 A1 | 4/2013 | Kostrzewski |
| 2013/0098965 A1 | 4/2013 | Kostrzewski et al. |
| 2013/0098966 A1 | 4/2013 | Kostrzewski et al. |
| 2013/0098968 A1* | 4/2013 | Aranyi .............. A61B 17/068 227/177.1 |
| 2013/0199327 A1 | 8/2013 | Park et al. |
| 2013/0245676 A1 | 9/2013 | Cappola |
| 2013/0304115 A1 | 11/2013 | Miyamoto |
| 2014/0224856 A1 | 8/2014 | Smith et al. |
| 2014/0276949 A1 | 9/2014 | Staunton et al. |
| 2014/0361068 A1 | 12/2014 | Aranyi et al. |
| 2015/0047451 A1* | 2/2015 | Kwon .............. A61B 17/29 74/490.05 |
| 2015/0083738 A1 | 3/2015 | Kasvikis et al. |
| 2015/0196996 A1 | 7/2015 | Nelson et al. |
| 2015/0342605 A1 | 12/2015 | Abbott et al. |
| 2015/0374396 A1 | 12/2015 | Strobl et al. |
| 2016/0058441 A1 | 3/2016 | Morgan et al. |
| 2016/0166250 A1 | 6/2016 | Marczyk |
| 2016/0270781 A1 | 9/2016 | Scirica |
| 2016/0270786 A1 | 9/2016 | Scirica |
| 2017/0000485 A1 | 1/2017 | Shelton et al. |
| 2017/0172577 A1 | 6/2017 | Wenchell et al. |
| 2017/0281177 A1 | 10/2017 | Harris et al. |
| 2017/0281184 A1 | 10/2017 | Shelton et al. |
| 2017/0281220 A1 | 10/2017 | Hibner et al. |
| 2018/0078354 A1 | 3/2018 | Cardinale et al. |
| 2018/0168599 A1 | 6/2018 | Bakos et al. |
| 2018/0289370 A1 | 10/2018 | Amariglio et al. |
| 2018/0310935 A1 | 11/2018 | Wixey |
| 2018/0317915 A1 | 11/2018 | Mcdonald |
| 2018/0368832 A1 | 12/2018 | Marecki et al. |
| 2019/0099182 A1 | 4/2019 | Bakos et al. |
| 2020/0008801 A1 | 1/2020 | Somekh et al. |
| 2020/0015818 A1 | 1/2020 | Amariglio et al. |
| 2020/0093486 A1 | 3/2020 | Somekh et al. |
| 2020/0222046 A1 | 7/2020 | Somekh et al. |
| 2021/0007740 A1 | 1/2021 | Marecki et al. |
| 2021/0212682 A1 | 7/2021 | Marecki et al. |
| 2021/0346016 A1 | 11/2021 | Marecki |
| 2022/0133314 A1 | 5/2022 | Li |
| 2022/0183689 A1 | 6/2022 | Marecki et al. |
| 2023/0233206 A1 | 7/2023 | Marecki et al. |
| 2023/0255626 A1 | 8/2023 | Marecki et al. |
| 2024/0023959 A1 | 1/2024 | Marecki |

FOREIGN PATENT DOCUMENTS

| | | |
|---|---|---|
| CN | 101965156 B | 12/2012 |
| CN | 108556696 B | 4/2024 |
| EP | 1563791 A1 | 8/2005 |
| EP | 1563792 A1 | 8/2005 |
| EP | 1563794 A1 | 8/2005 |
| EP | 1709911 A1 | 10/2006 |
| EP | 1021130 B1 | 11/2006 |
| EP | 1908410 A1 | 4/2008 |
| EP | 2253277 A1 | 11/2010 |
| EP | 2253278 A1 | 11/2010 |
| EP | 1536792 B1 | 9/2013 |
| EP | 2586382 A3 | 9/2013 |
| EP | 2662033 A1 | 11/2013 |
| EP | 2073718 B1 | 8/2014 |
| EP | 2777530 A1 | 9/2014 |
| EP | 2886020 A1 | 6/2015 |
| EP | 2886071 A1 | 6/2015 |
| EP | 2484290 B1 | 7/2015 |
| EP | 2311385 B1 | 5/2017 |
| EP | 2807982 B1 | 8/2017 |
| EP | 3222221 A1 | 9/2017 |
| WO | 2016107586 A1 | 7/2016 |

OTHER PUBLICATIONS

Final Office Action received in U.S. Appl. No. 16/027,579 dated Dec. 11, 2020, 19 pages.
Final Office Action received in U.S. Appl. No. 16/027,579 dated Dec. 20, 2021, 20 pages.
Final Office Action received in U.S. Appl. No. 17/033,210 dated Aug. 25, 2022, 12 pages.
Final Office Action received in U.S. Appl. No. 17/669,683 dated Jun. 4, 2024, 19 pages.
Final Office Action received in U.S. Appl. No. 18/129,284 dated Aug. 7, 2024, 8 pages.
Final Office Action received in U.S. Appl. No. 18/129,294 dated Aug. 7, 2024, 8 pages.
International Search Report and Written Opinion dated Apr. 7, 2020 for PCT Application No. PCT/US2020/013694 filed Jan. 15, 2020, 8 pages.
International Search Report and Written Opinion dated Jun. 18, 2018 for PCT Application No. PCT/US2018/025988 filed Apr. 4, 2018, 8 pages.
International Search Report and Written Opinion dated Oct. 22, 2018 for PCT Application No. PCT/US2018/038909 filed Jun. 22, 2018, 10 pages.
International Search Report and Written Opinion dated Oct. 4, 2019 for PCT Application No. PCT/US2019/040315 filed Jul. 2, 2018, 9 pages.
International Search Report and Written Opinion received in PCT Application No. PCT/US21/13226 dated Mar. 26, 2021, 8 pages.
International Search Report and Written Opinion received in PCT Application No. PCT/US21/25899 dated Jun. 28, 2021, 6 pages.
International Search Report and Written Opinion received in PCT Application No. PCT/US23/12664 dated Mar. 15, 2023, 9 pages.
Non Final Office Action received in U.S. Appl. No. 16/027,579 dated Jul. 22, 2021, 17 pages.
Non Final Office Action received in U.S. Appl. No. 16/027,579 dated Jun. 12, 2020, 16 pages.
Non Final Office Action received in U.S. Appl. No. 16/743,317 dated Aug. 20, 2021, 12 pages.
Non Final Office Action received in U.S. Appl. No. 17/033,210 dated Mar. 4, 2022, 15 pages.

(56) References Cited

OTHER PUBLICATIONS

Non Final Office Action received in U.S. Appl. No. 17/382,657 dated Jan. 31, 2023, 11 pages.
Non Final Office Action received in U.S. Appl. No. 17/669,683 dated Dec. 22, 2022, 18 pages.
Non Final Office Action received in U.S. Appl. No. 18/129,284 dated May 1, 2024, 13 pages.
Non Final Office Action received in U.S. Appl. No. 18/129,294 dated May 1, 2024, 13 pages.
Non Final Office Action received in U.S. Appl. No. 18/479,593 dated Aug. 6, 2024, 12 pages.
Non-Final Office Action received in U.S. Appl. No. 15/631,429 dated Aug. 29, 2019, 16 pages.
Notice of Allowance received in U.S. Appl. No. 15/631,429 dated Oct. 29, 2020, 9 pages.
Notice of Allowance received in U.S. Appl. No. 16/027,579 dated Mar. 14, 2022, 8 pages.
Notice of Allowance received in U.S. Appl. No. 16/743,317 dated Dec. 17, 2021, 8 pages.
Notice of Allowance received in U.S. Appl. No. 16/845,217 dated Jun. 9, 2021, 8 pages.
Notice of Allowance received in U.S. Appl. No. 17/033,210 dated Mar. 8, 2023, 8 pages.
Notice of Allowance received in U.S. Appl. No. 17/382,657 dated May 23, 2023, 7 pages.
Notice of Allowance received in U.S. Appl. No. 17/689,549 dated Jul. 31, 2023, 11 pages.
Restriction Requirement mailed in U.S. Appl. No. 15/631,429 dated Jul. 29, 2019, 6 pages.
Restriction Requirement received in U.S. Appl. No. 16/027,579 dated Mar. 16, 2020, 6 pages.
Notice of Allowance received in U.S. Appl. No. 18/129,284 dated Jan. 22, 2025, pp. all.

\* cited by examiner

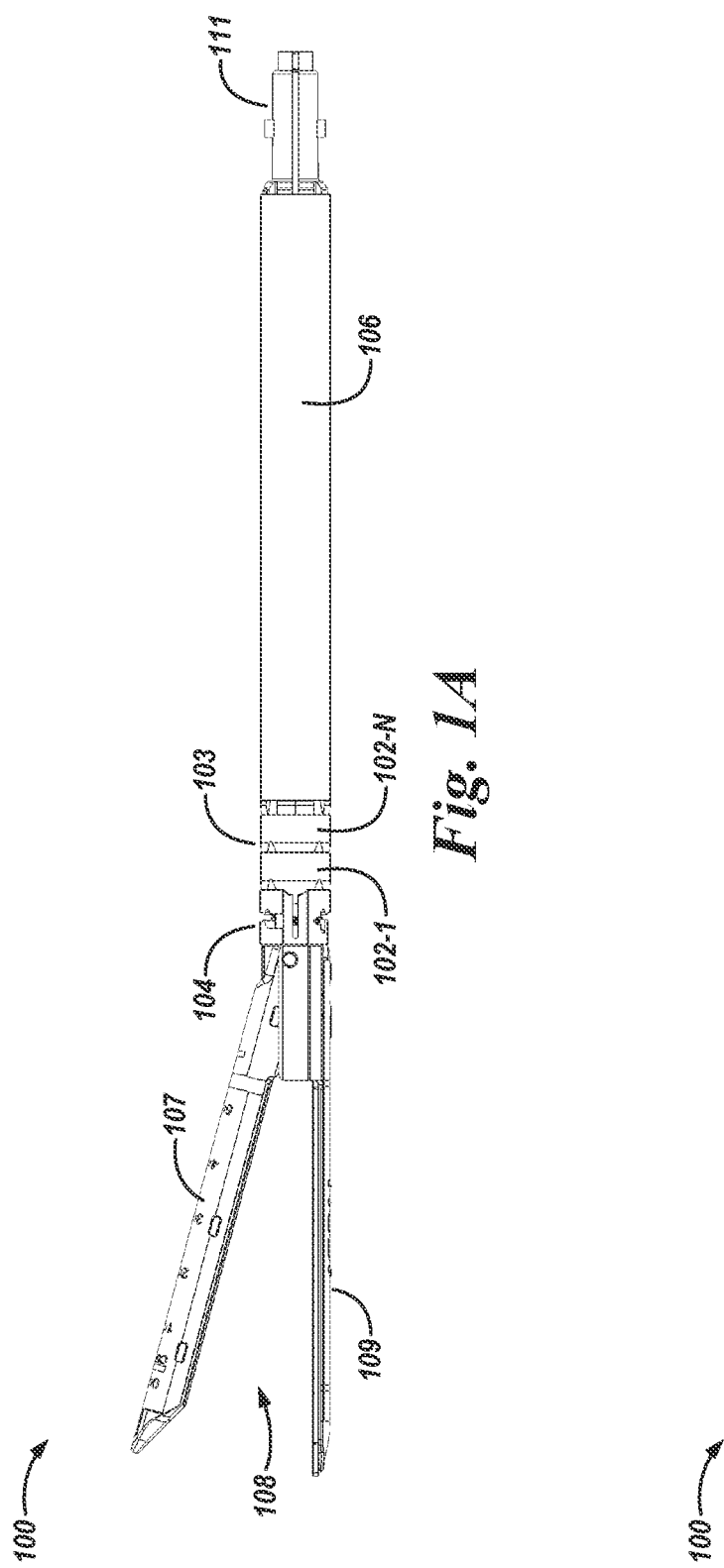
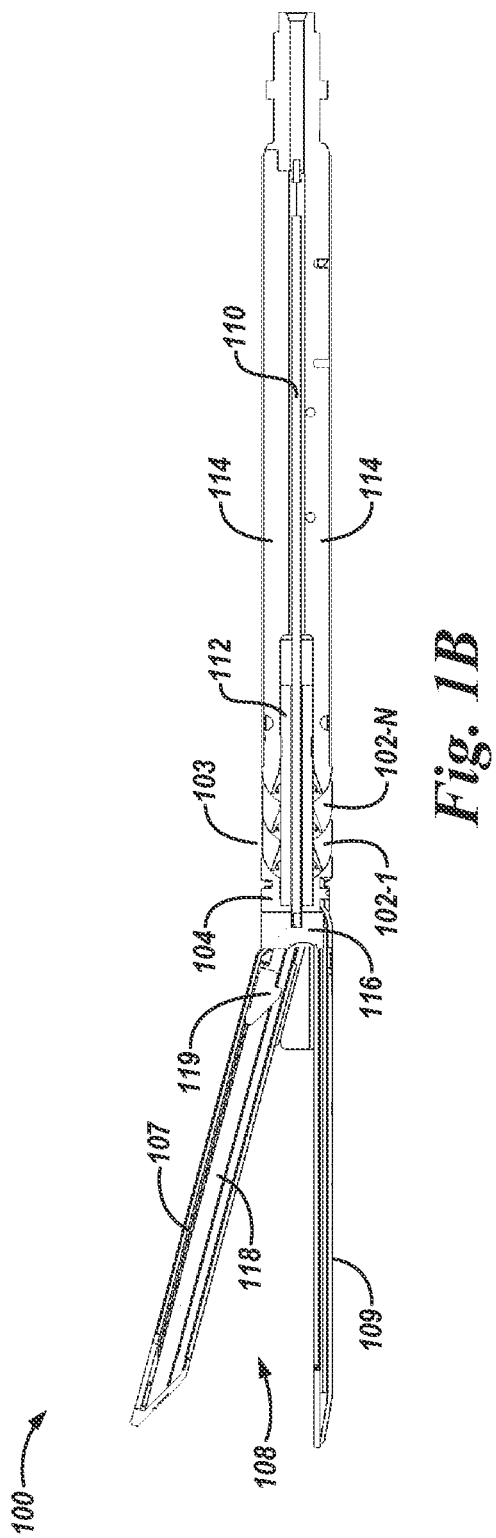

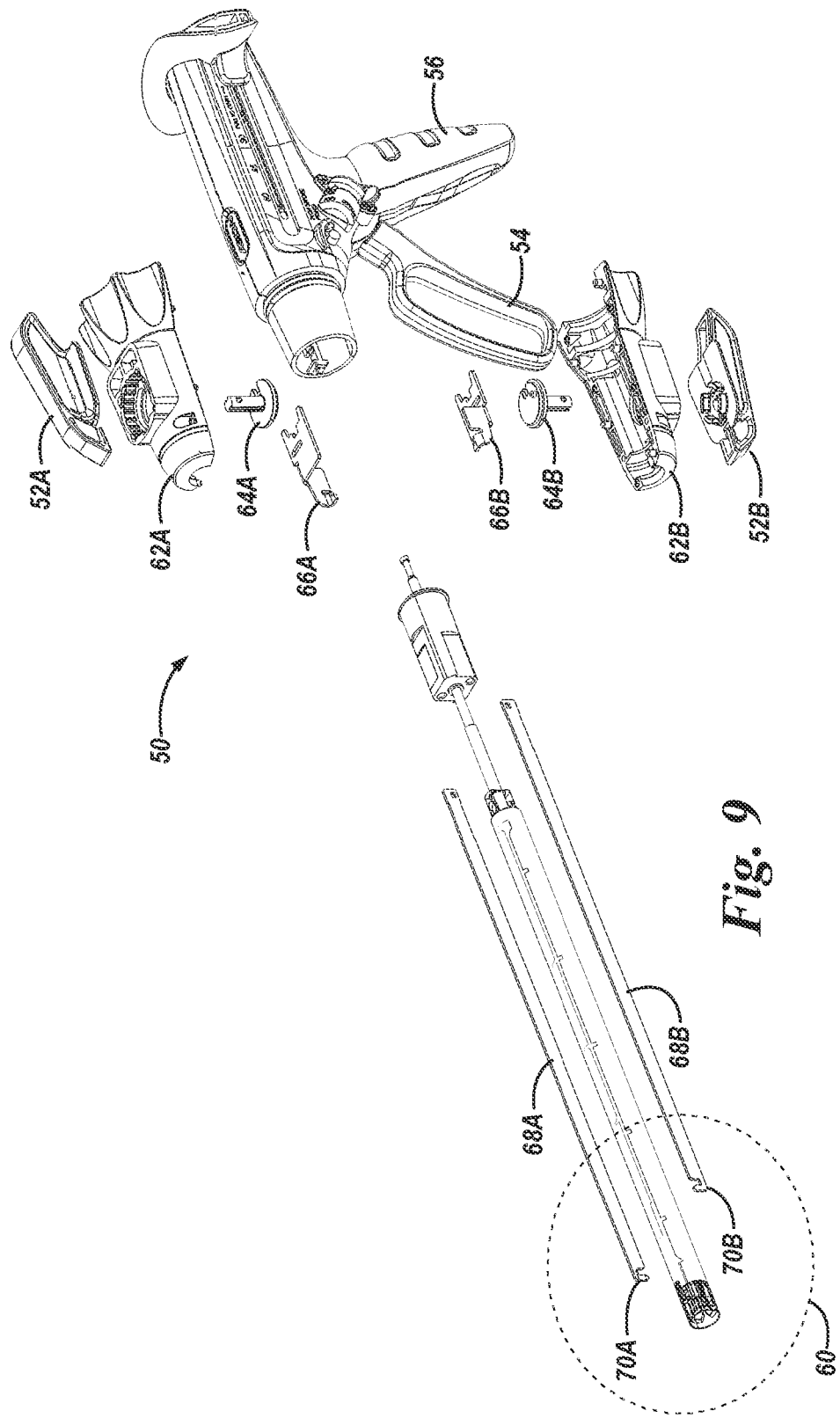

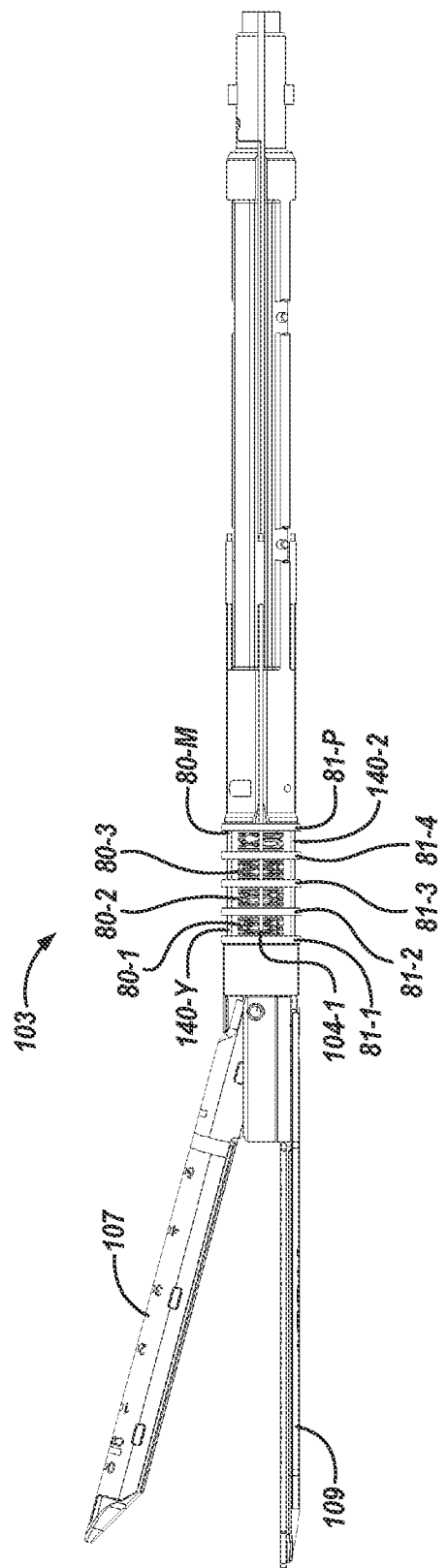

MULTIDIRECTIONAL APPARATUS

RELATED APPLICATIONS

This application is a Continuation of U.S. Patent Application Ser. No. 17/689,549, filed Mar. 8, 2022, now U.S. Pat. No. 11,844,523, which is a Continuation of U.S. Patent Application Ser. No. 16/743,317, filed Jan. 15, 2020, now U.S. Pat. No. 11,298,131, which are hereby incorporated herein by reference in their entireties.

TECHNICAL FIELD

The present disclosure relates generally to medical devices, particularly to a multidirectional apparatus for a surgical stapler, a handle assembly for a surgical stapler, or other medical device, and more particularly, for providing multidirectional articulation of the medical device.

BACKGROUND

Surgical staplers are used in a variety of medical procedures. Generally, a handle or drive assembly is connected to a staple containing unit called a reload cartridge. A surgical stapler is a fastening device used to clamp tissue between opposing jaw structures and to join the tissue using surgical fasteners. A stapler reload apparatus can include two elongated members used to clamp the tissue. One of the elongated members can include one or more staples and the other elongated member can include an anvil that can be used to form a staple when it is driven from the reloadable cartridge. A surgical stapler can receive one or more reloadable cartridges. An example of reloadable cartridges can include having rows of staples having a linear length. A row of staples can have a linear length between 30 mm and 60 mm, for example. A staple can be ejected by actuation of a movable handle member that is a part of the surgical handle assembly of the surgical stapler. A staple can be ejected through the use of a robotic or remotely controlled driver that is part of a drive assembly.

SUMMARY

In one embodiment, a surgical instrument such as a reload cartridge is provided. In some embodiments, the reload cartridge comprises two elongated members of a jaw mechanism moveable between an open and closed position. A slide element (e.g., an I-beam) is provided to, when moved in a distal direction, cause the jaw mechanism to move from an open to a closed position. When the I-beam is moved proximally, the jaw mechanism will move from a closed position to an open position. One of the elongated members of the jaw mechanism can include one or more staples and the other elongated member can include an anvil that can be used to form staples upon delivery. A thrust wire can be moved distally causing the I-beam to move distally which can cause a stapling wedge to move and deliver staples.

To assist the physician or user in positioning the stapler at a desired location within the body, an articulation joint is provided. Many articulation joints only allow articulation in one plane. In one embodiment, the disclosed articulation joint allows the jaw mechanism to be articulated in two planes—up/down and left/right. By using a number of planes, the jaw mechanism can be articulated 360° relative to the longitudinal axis. In some examples, the jaw mechanism can articulate in a cone of 120°. For example, from the longitudinal axis, the jaw mechanism can articulate 60° or more in a first direction and 60° or more in a second direction.

In one embodiment, the articulation joint can be formed from nested hemispherical articulation elements. In another embodiment, the articulation joint is formed from a composite shaft. In another embodiment, the articulation joint can be formed from spring elements adjacent to one or more wire guides.

BRIEF DESCRIPTION OF THE DRAWINGS

FIG. 1A is a side view of a multidirectional apparatus in accordance with a number of embodiments of the present disclosure.

FIG. 1B is a section view of a multidirectional apparatus in accordance with a number of embodiments of the present disclosure.

FIG. 9 is an exploded view of a surgical handle assembly in accordance with an embodiment of the present disclosure.

FIG. 10A is a side view of a multidirectional apparatus in accordance with a number of embodiments of the present disclosure.

DETAILED DESCRIPTION

Figure 2:
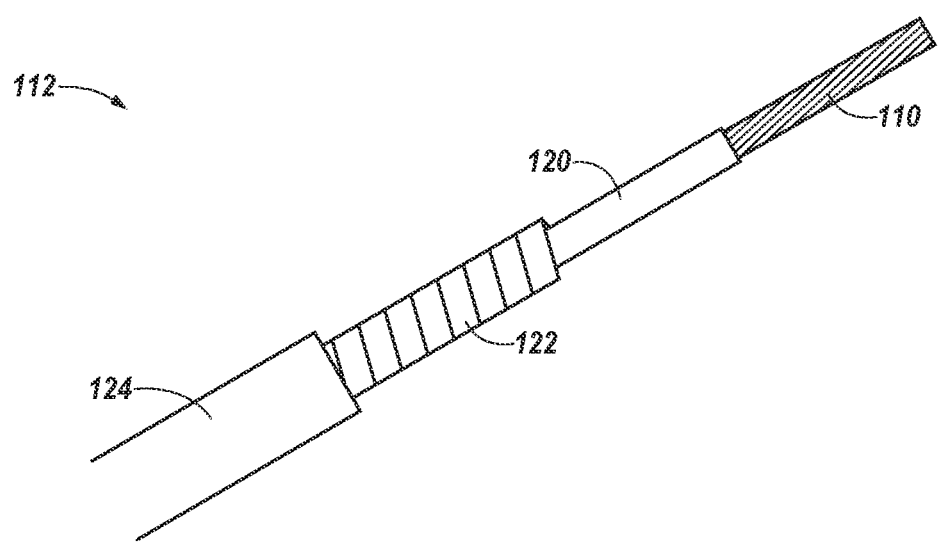
FIG. 2 is a side view of a sheath in accordance with a number of embodiments of the present disclosure.

The present disclosure includes a multidirectional apparatus for use with a surgical handle assembly. The surgical handle assembly can be a manual or electrically driven unit. In some embodiments, the surgical handle assembly is driven by a robot or a remotely controlled unit.

In some examples, the multidirectional apparatus can be a stapler reload apparatus. When used in open or minimally invasive surgery, the physician may need to articulate the jaw mechanism of the stapler or move the jaw mechanism away from the longitudinal axis of the reload apparatus, to better position the jaw mechanism at the desired location. In embodiments of the present disclosure, an articulation joint is provided that allows for articulation of the jaw mechanism in all directions, or 360° away from the longitudinal axis of the multidirectional apparatus. In some examples, the jaw mechanism can articulate in a cone of 120°. For example, from the longitudinal axis, the jaw mechanism can articulate 60° in a first direction and 60° in a second direction.

In a number of embodiments, the multidirectional apparatus can be part of the surgical handle assembly. For example, the multidirectional apparatus can be permanently coupled to the handle assembly and a staple cartridge can be loaded (e.g., inserted) and/or unloaded (e.g., removed) from the multidirectional apparatus. In other embodiments, the multidirectional apparatus can be temporarily coupled to the surgical handle assembly and can be loaded and/or unloaded from the surgical handle assembly.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

As used herein, designators such as "X", "Y", "N", "M", "P", "Q", etc., particularly with respect to reference numerals in the drawings, indicate that a number of the particular feature so designated can be included. It is also to be understood that the terminology used herein is for the purpose of describing particular embodiments only and is not intended to be limiting. As used herein, the singular forms "a", "an", and "the" can include both singular and plural referents, unless the context clearly dictates otherwise. In addition, "a number of", "at least one", and "one or more" (e.g., a number of articulation elements) can refer to one or more articulation elements, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of the movable handle member, handle assembly, and/or multidirectional apparatus, as appropriate to the context.

As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1A is a side view of a multidirectional apparatus 100 in accordance with a number of embodiments of the present disclosure. The multidirectional apparatus 100 can include an articulation joint 103, a connector 104, a shaft 106, a jaw mechanism 108, and a connector 111.

The multidirectional apparatus 100 can be connected to a surgical handle assembly (e.g., surgical handle assembly 50 in FIG. 8) via connector 111. In some examples, the multidirectional apparatus 100 can be a stapler reload apparatus. A stapler reload apparatus can be a disposable loading unit that is releasably secured to a distal end of an elongated body of a surgical handle assembly. The connector 111 can connect the multidirectional apparatus 100 to the surgical handle assembly and/or a drive assembly. The drive assembly can include a robotic or remotely controlled driver.

As shown in the example of FIG. 1A, the multidirectional apparatus 100 can include a jaw mechanism 108. The jaw mechanism 108 can include a first elongated member 107 and a second elongated member 109 coupled at a proximal pivot point. The jaw mechanism 108 can be in a closed position when the first elongated member 107 and the second elongated member 109 are clamping tissue and/or contacting each other. The jaw mechanism 108 can be in an open position when the first elongated member 107 and the second elongated member 109 are not clamping tissue and/or are not in contact with each other. In FIG. 1A, the jaw mechanism 108 is in an open position.

FIG. 1B is a section view of the multidirectional apparatus 100 in accordance with a number of embodiments of the present disclosure. As shown in FIG. 1B, elongated member 107 can include a stapling wedge 119 for delivering staples. The staples and/or staple cartridges can be contained in elongated member 107. Elongated member 109 can include an anvil for forming the staples. Elongated member 107 and elongated member 109 can move or one of the elongated members 107 or 109 can be stationary.

The force needed to close elongated members 107 and 109 to clamp onto tissue and the force needed to deliver staples is provided via thrust wire 110. The thrust wire 110 is used to transmit force from a proximal end of the multidirectional apparatus 100 to the distal end. The proximal end of thrust wire 110 is positioned near the proximal end of multidirectional apparatus 100 so that the surgical handle assembly and/or the drive assembly can interact with the multidirectional apparatus 100 to move the thrust wire 110 in the distal and proximal directions. The distal end of thrust wire 110 is connected to I-beam 116.

As shown, at the proximal end of jaw mechanism 108 is I-beam 116. When moved proximally by thrust wire 110, I-beam 116 causes elongated members 107 and 109 of the jaw mechanism 108 to move from the closed position to the open position. When moved distally by thrust wire 110, I-beam 116 can cause elongated members 107 and 109 of the jaw mechanism 108 to move from the open position to the closed position. Further, distal movement of the thrust wire 110 and I-beam 116 can move stapling wedge 119 in the distal direction which can cause one or more staples to be ejected from the elongated member 107.

Figure 5:
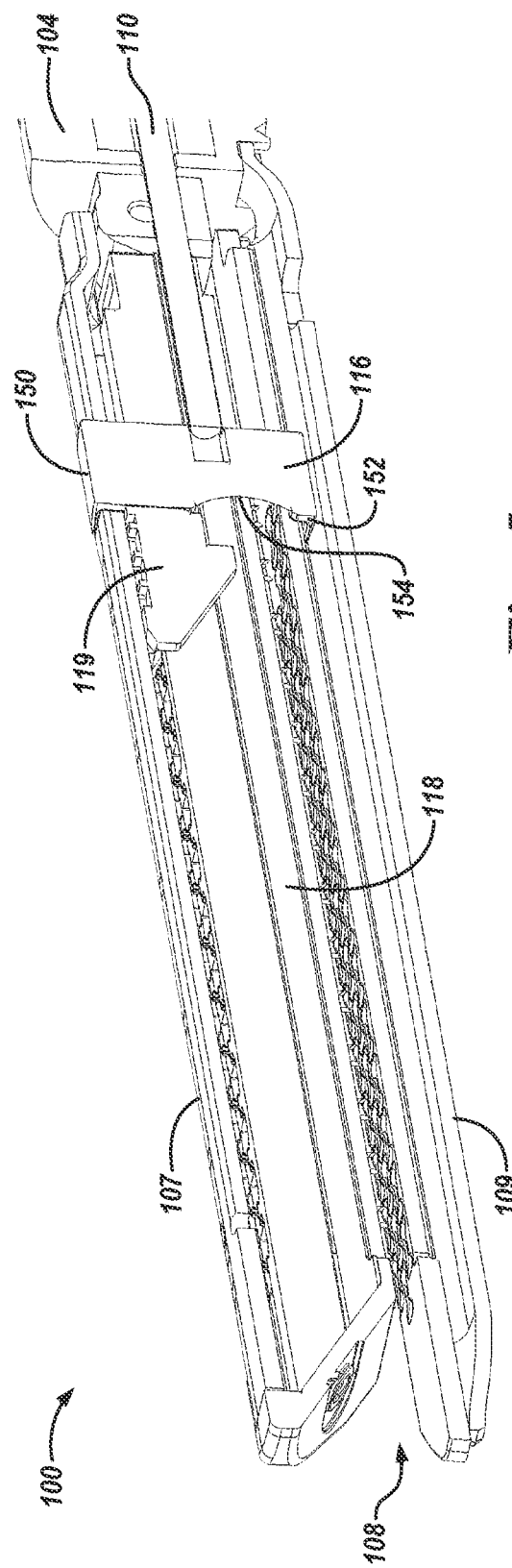
FIG. 5 is a section view of a multidirectional apparatus in accordance with a number of embodiments of the present disclosure.

I-beam 116 can have a top lateral structure (e.g., top lateral structure 150 in FIG. 5) and a bottom lateral structure (e.g., bottom lateral structure 152 in FIG. 5). The top and bottom lateral structures can hold elongated members 107 and 109 in the clamped position so that as staples are ejected, the anvil is held firmly in place and the staples are formed. As I-beam 116 is moved in a distal direction, the distal edge (e.g., distal edge 154 in FIG. 5) of I-beam 116 cuts the tissue situated between the rows of staples.

Hypo tube 118 is located in elongated member 107. The thrust wire 110 can be positioned within the shaft 106, the central lumen (e.g., central lumen 130 in FIG. 3A), and/or the hypo tube 118. The hypo tube 118 can provide support for the thrust wire 110 to prevent the thrust wire 110 from bowing and/or buckling when the thrust wire 110 is moved in the distal direction. In some examples, the hypo tube 118 can include a slot to allow the I-beam 116 to span a midplane of the multidirectional apparatus 100.

The articulation joint 103 can be positioned at the distal end of shaft 106. The articulation joint 103 can include one or more articulation members 102-1, . . . , 102-N. While only articulation member 102-1 and articulation member 102-N are shown, any number of articulation members 102-1, . . . , 102-N can be used.

The articulation joint 103 including the articulation members 102-1 and 102-N allow for articulation of the jaw mechanism 108 in any direction as will be explained below. The connector 104 is positioned at the distal end of articulation joint 103. Jaw mechanism 108 is connected to the distal end of connector 104.

Shaft 106 includes a proximal and distal end and a longitudinal axis. In some examples, the shaft 106 can also include inserts 114. Inserts 114 are provided to take up space between sheath (e.g., sheath 112 in FIG. 2) and shaft 106 so that as force is applied to thrust wire 110, the thrust wire 110 and sheath cannot bend, buckle, and/or bow.

FIG. 2 is a side view of a sheath 112 in accordance with a number of embodiments of the present disclosure. As shown in FIG. 2, thrust wire 110 can be contained within sheath 112. In a number of embodiments, sheath 112 is a Bowden sheath or similar product. In some examples, the sheath 112 comprises the thrust wire 110 (e.g., an incompressible inner member), an inner lubricious liner 120, an outer housing 122, and/or a protective covering 124. Thrust wire 110 can be made from a wire, a braided wire, a helical winding, a sheaf of wires, a hollow tube, or any combination thereof. Lubricious inner liner 120, which reduces friction between the moveable thrust wire 110 and outer housing 122, can be made from polytetrafluoroethylene (PTFE), polyethylene, polyamide, or other similar polymers. Outer housing 122 can be made from a solid or slotted tube or a helical winding. In some embodiments, outer housing 122 is made from a helical winding so as to impart flexibility to the sheath 112. The winding can be made with round or flat wire. Protective covering 124 can be made from polyvinyl chloride, polyurethane, or any similar polymer or material. While shown here with four layers, in some embodiments, the sheath 112 may comprise just the thrust wire 110 and in other embodiments, the thrust wire 110 and an exterior layer. In some embodiments, thrust wire 110 is made from stainless steel although it can be made from super-elastic alloys such as nitinol.

As shown in the embodiments herein, the cross-section of the thrust wire 110 can be round. In other embodiments, the cross-section of the thrust wire 110 may not be round but will be nearly round. A round structure does not have a preferential axis of bending. In embodiments where a preferential axis is desired, the cross-section of the thrust wire 110 may be oval or other non-round shape. In some embodiments, the cross-section of the thrust wire 110 may be round with a small bump in a cross-section view. This small raised structure, a key, may run the entire length of the thrust wire 110. The key can be constructed and arranged to interact with the other components of the shaft 106 to prevent rotation of the thrust wire 110 during use of the multidirectional apparatus. Preferably the key would be sized and shaped so that it only minimally affects the bending motion of the thrust wire 110.

Figure 3A:
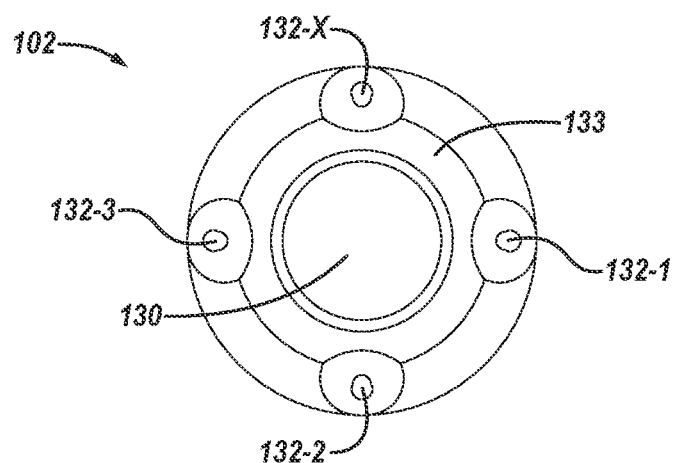
FIG. 3A is a top view of an articulation element in accordance with a number of embodiments of the present disclosure.
Figure 3B:
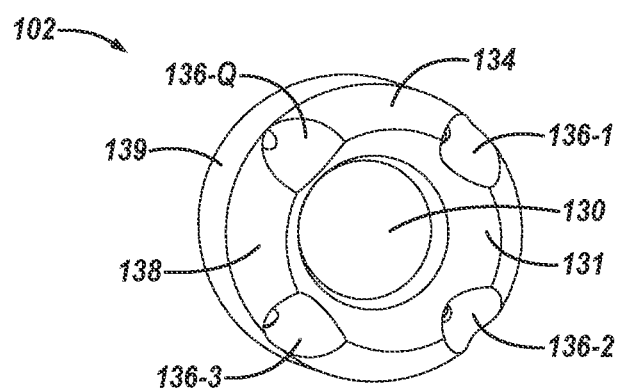
FIG. 3B is a perspective view of an articulation element in accordance with a number of embodiments of the present disclosure.
Figure 3C:
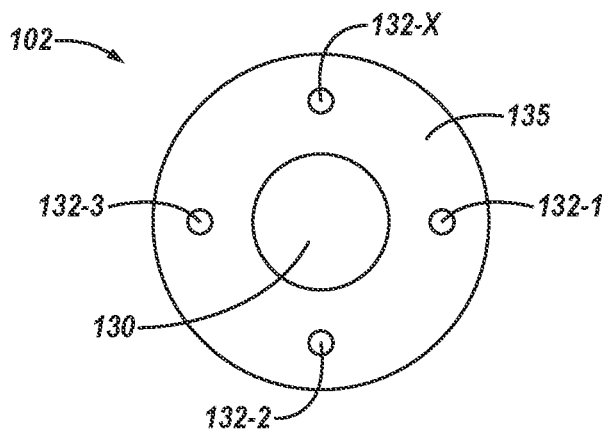
FIG. 3C is a bottom view of an articulation element in accordance with a number of embodiments of the present disclosure.

FIGS. 3A, 3B, and 3C show three views of an articulation element 102. In general, the articulation element 102 has a hollow cylindrical proximal end 139 with a central lumen 130, a wall 131 surrounding the central lumen 130, and a hemispherical distal end 138. Sheath 112 can be positioned within central lumen 130.

The distal end of the articulation element 102 includes exterior slope 134 on the outer diameter which results in a hemispherical shape. The distal end 138 also has an internal slope 133 on the inner diameter. As shown in FIG. 3C, the proximal end has a cylindrical outer diameter and internal slope 135. Slope 135 is generally in the shape of a hemisphere so that a distal end of an adjacent articulation element can nest within the proximal end. For example, the cylindrical proximal end of a second articulation element (e.g., articulation element 102-2 in FIG. 4) covers the hemispherical distal end of a first articulation element (e.g., articulation element 102-1 in FIG. 4) such that the central lumen 130 of the first articulation element and the central lumen 130 of the second articulation element are not exposed in response to movement (e.g., articulation) of the first articulation element and/or the second articulation element.

In some embodiments there are a number of lumens 132-1, 132-2, 132-3, . . . , 132-X in the wall 131 of each articulation element 102. Pull wires (e.g., pull wires 140-1, 140-2, 140-3, . . . , 140-Y in FIG. 4) are situated within each of the number of lumens 132-1, . . . , 132-X. Grooves 136-1, 136-2, 136-3, . . . , 136-Q can be provided to allow the pull wires room to accommodate the full range of articulation.

Figure 4A:
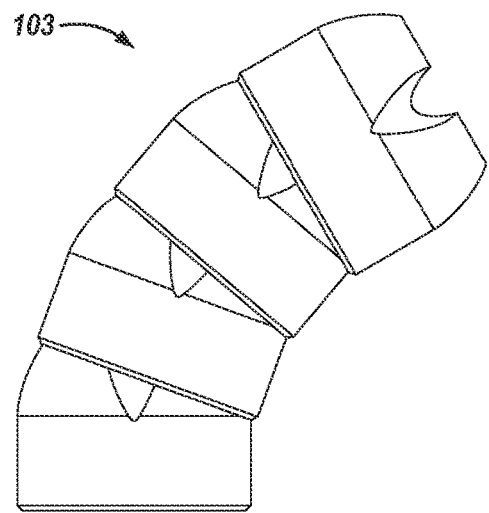
FIG. 4A is a top view of an articulation joint in an articulated position in accordance with a number of embodiments of the present disclosure.
Figure 4B:
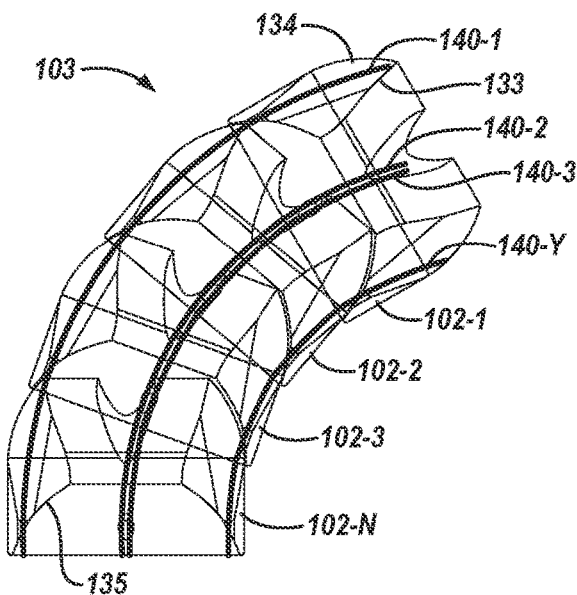
FIG. 4B is a transparent view of an articulation joint in an articulated position in accordance with a number of embodiments of the present disclosure.
Figure 4C:
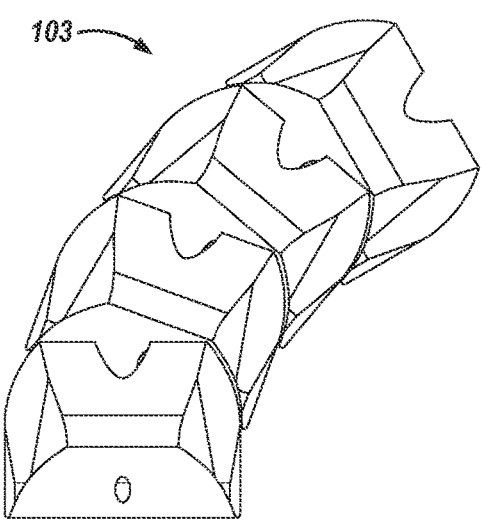
FIG. 4C is a section view of an articulation joint in an articulated position in accordance with a number of embodiments of the present disclosure.

FIGS. 4A, 4B, and 4C show three views of an articulation joint 103 in an articulated position. In each view, there are a number of articulation elements 102-1, 102-2, 102-3, . . . , 102-N and a number of pull wires 140-1, 140-2, 140-3, . . . , 140-Y. While each view includes four articulation elements 102-1, . . . , 102-N and four pull wires 140-1, . . . , 140-Y, two, three, four, five, six, or more could be used.

When the articulation joint 103 is assembled, a distal end 138 of articulation element 102-2 is positioned within proximal end 139 of articulation element 102-1, a distal end 138 of articulation element 102-3 is positioned within proximal end 139 of articulation element 102-2, and a distal end 138 of articulation element 102-N is positioned within proximal end 139 of articulation element 102-3.

As one or more of the pull wires 140-1 and 140-Y is put under tension (e.g., pulled in a proximal direction), one or more of the number of articulation elements 102-1, . . . , 102-N articulate and the jaw mechanism 108 moves away from the longitudinal axis of multidirectional apparatus 100 in the direction of the wire that is under tension. When one pull wire of the number of pull wires 140-1 and 140-Y is pulled and put under tension, a different pull wire of the number of pull wires 140-1 and 140-Y may be under compression and may move distally. For example, pull wire 140-1, 180° away from pull wire 140-Y, which is under tension, will be under compression and will move distally.

If two pull wires 140-1 and 140-Y are used and are placed 180° apart, articulation may be limited to only one plane. If using two pull wires 140-1 and 140-2, they can be placed 90° apart to allow the articulation joint 103 to move in more than one plane. For example, a first pull wire 140-1 and a first pull wire lumen 132-1 can be located approximately one-fourth of the way around a circumference of the wall 131 surrounding the central lumen 130 of each of the articulation elements 102-1, . . . , 102-N and a second pull wire 140-2 and a second pull wire lumen 132-2 can be located approximately two-fourths of the way around a circumference of the wall 131 surrounding the central lumen 130 of each of the articulation elements 102-1, . . . , 102-N. When using three or more wires, they can be evenly spaced around the circumference of the articulation joint 103. For example, when the articulation joint 103 includes four pull wires 140-1, . . . , 140-Y and four pull wire lumens 132-1, . . . , 132-X, each pull wire 140-1, . . . , 140-Y and each pull wire lumen 132-1, . . . , 132-X can be located approximately one-fourth of the way around the circumference of the wall 131 surrounding the central lumen 130 of each of the articulation elements 102-1, . . . , 102-N.

In the embodiment shown, wire 140-Y has been pulled or put under tension and 140-1 has been put under compression and has moved distally. In this drawing, the function of the distal and proximal internal slopes 133 and 135 are shown.

While not shown in FIG. 4, when assembled, the articulation assembly will include sheath 112 situated within central lumen 130. In some embodiments, when articulated, it is important that the central lumen 130 maintains a minimum effective diameter equal to the diameter of sheath 112 and that no gaps appear between the proximal end of one articulation element 102-1 and the distal end of an adjacent element 102-2. For example, the minimum effective diameter can be maintained even when articulation element 102-1 articulates relative to articulation element 102-2. The proximal and distal interior slopes accommodate articulation without interfering with sheath 112.

FIG. 5 is a section view of multidirectional apparatus 100 in accordance with a number of embodiments of the present disclosure. This view shows the multidirectional apparatus 100 in the closed position where a number of the staples have already been delivered. Connector (or hinge block) 104 is shown at the proximal end. Thrust wire 110 extends through connector 104, through hypo tube 118 and is connected to I-beam 116. As compression force is applied to thrust wire 110 it moves in a distal direction and lateral surfaces 150 and 152 of I-beam 116 interact with surfaces of elongated members 107 and 109 to move the two elongated members 107 and 109 to a closed position. As the I-beam 116 continues to move distally, it pushes stapling wedge 119 in a distal direction. Stapling wedge 119 pushes staples in a lateral direction toward the anvil on elongated member 109, which causes the staples to form. I-beam 116 also contains cutting edge 154 which cuts the tissue (not shown) as the staples are applied.

Hypo tube 118 is provided to provide columnar support to thrust wire 110. While the thrust wire 110 is relatively incompressible in a longitudinal direction, it is flexible and thus has substantially less strength in a lateral direction. In order to efficiently transfer force to I-beam 116, thrust wire 110 is surrounded by hypo tube 118. In a number of embodiments, the hypo tube 118 can include two slots located 180° apart. The slots can be sized so that I-beam 116 can move or translate within the slots. In some examples, hypo tube 118 has a cylindrical distal end that is not slotted.

Figure 6A:
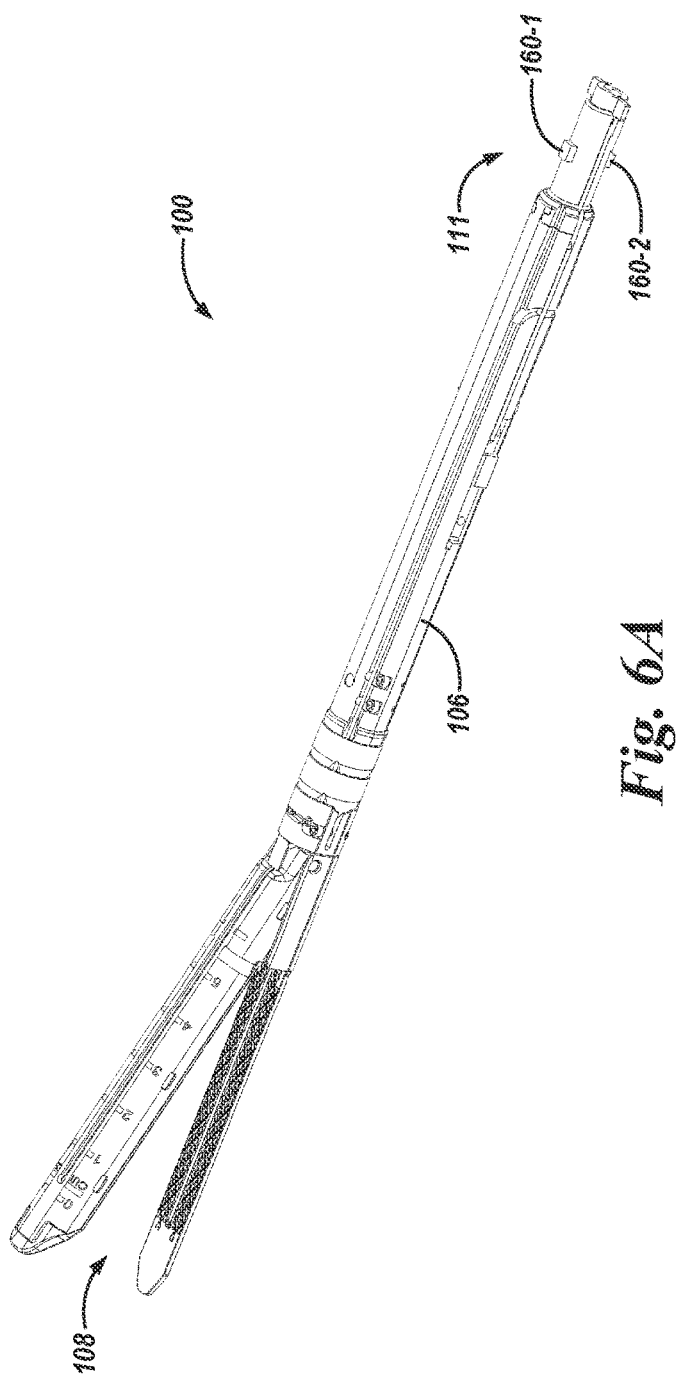
FIG. 6A is a perspective view of a multidirectional apparatus in accordance with a number of embodiments of the present disclosure.

FIG. 6A is a perspective view of multidirectional apparatus 100 in accordance with a number of embodiments of the present disclosure. The proximal portion 111 of the multidirectional apparatus 100, is shown with tabs 160-1 and 160-2. The tabs 160-1 and 160-2 can interact with a surgical handle assembly (e.g., surgical handle assembly 50 in FIG. 9) to allow the user to articulate the jaw mechanism 108.

Figure 6B:
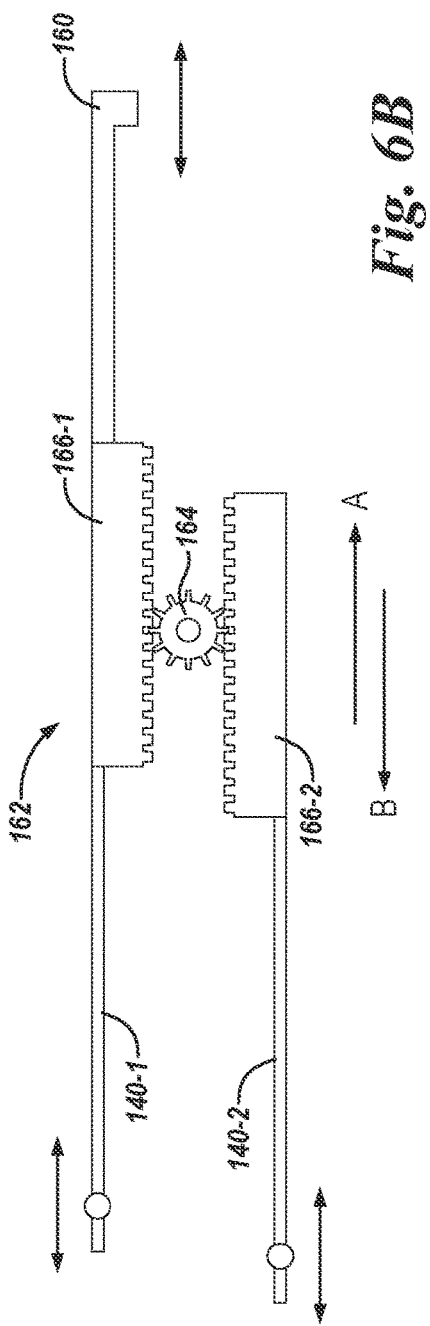
FIG. 6B is a perspective view of a mechanism for advancing and/or retracting pull wires in a multidirectional apparatus in accordance with a number of embodiments of the present disclosure.

FIG. 6B is a perspective view of a mechanism 162 for advancing and/or retracting pull wires 140-1, . . . , 140-2 in multidirectional apparatus 100 in accordance with a number of embodiments of the present disclosure. The mechanism 162 can be one of one or more rack and pinion mechanisms in shaft 106. The mechanism 162 can include pinion 164 and one or two racks 166-1 and 166-2. One of the racks 166-1 can be connected to a tab 160 on the proximal end of multidirectional apparatus 100. Rack 166-1 can be coupled to pull wire 140-1 and rack 166-2 can be connected to a pull wire 140-2. As tab 160 is moved proximally, in the direction of arrow A, rack 166-1 and pull wire 140-1 that are attached to tab 160 will be under tension and will also move in the direction of arrow A. Rack 166-2 and pull wire 140-2 that are on the other side of pinion 164, that are not connected to tab 160, will be under compression and will move distally, in the direction of arrow B.

As shown in FIG. 4, the distal ends of pull wires 140-1 and 140-2 are connected distal of the most distal articulation member 102-1. The pull wire 140-1 in FIG. 6B that is under tension will cause the articulation joint 103 to bend in the direction of the pull wire 140-1 that is under tension and will cause pull wire 140-2 on the other side of the mechanism 162 to be under compression. In some embodiments, multidirectional apparatus 100 will have two rack and pinion mechanisms 162 so that articulation of articulation joint 103 in all directions can be achieved. While this embodiment shows a rack and pinion mechanism 162, other mechanisms can be used as contemplated herein.

Figure 6C:
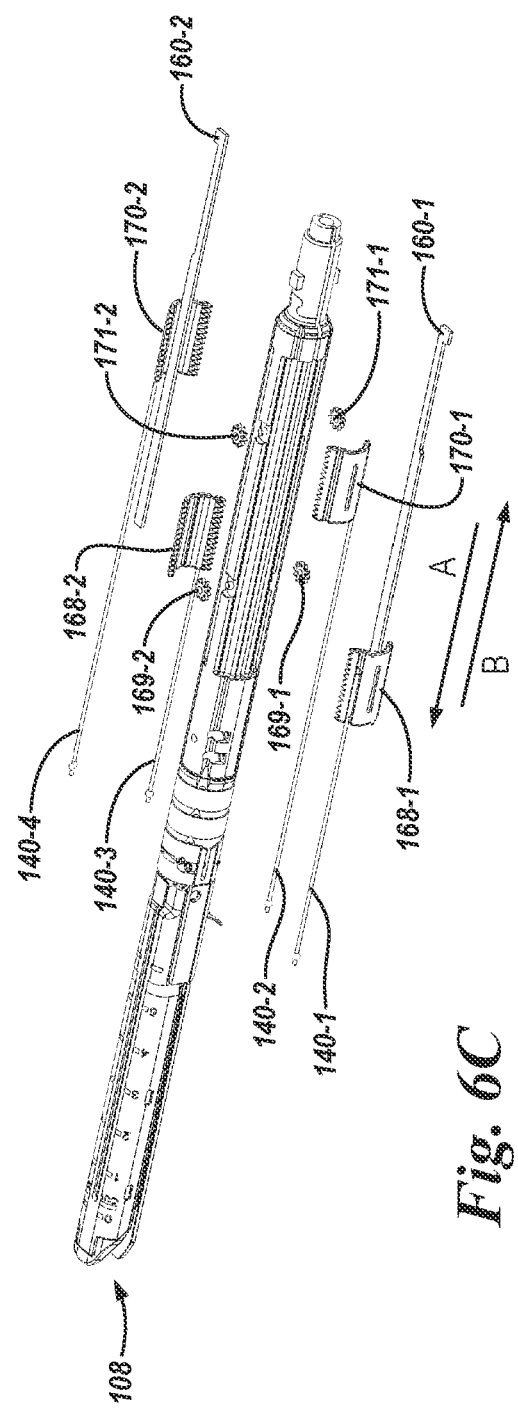
FIG. 6C is an exploded view of a mechanism for advancing and/or retracting pull wires in a multidirectional apparatus in accordance with a number of embodiments of the present disclosure.

FIG. 6C is an exploded view of a mechanism 162 for advancing and/or retracting pull wires 140-1, . . . , 140-Y in multidirectional apparatus 100. In this embodiment, there are a first pair of racks 168-1 and 168-2 and a first pair of pinions 169-1 and 169-2 for a first pair of pull wires 140-1 and 140-3. The pair of racks 168-1 and 168-2 are placed in the shaft 106 of the multidirectional apparatus 100 with pinions 169-1 and 169-2 positioned on either side of racks 168-1 and 168-2. Rack 168-1 is connected to tab 160-1. Rack 168-1 is attached to pull wire 140-1 and rack 168-2 is attached to pull wire 140-3.

As tab 160-1 is moved in a distal direction, shown as arrow A, rack 168-1 that is connected to tab 160-1 will also move in the distal direction, exerting compressive force on the pull wire 140-1 that is attached to rack 168-1. Rack 168-2 that is located opposite rack 168-1 will then move in a proximal direction, shown as arrow B, putting tension on pull wire 140-3 that is attached to rack 168-2. This movement will cause jaw mechanism 108 to move toward pull wire 140-3 that is under tension and away from pull wire 140-1 that is under compression.

This figure shows a second pair of racks 170-1 and 170-2, a second pair of pinions 171-1 and 171-2, and a second tab 160-2. The second pair of racks 170-1 and 170-2, the second pair of pinions 171-1 and 171-2, and the second tab 160-2 can operate in the same manner as the first pair of racks 168-1 and 168-2, the first pair of pinions 169-1 and 169-2, and the first tab 160-1.

Figure 6D:
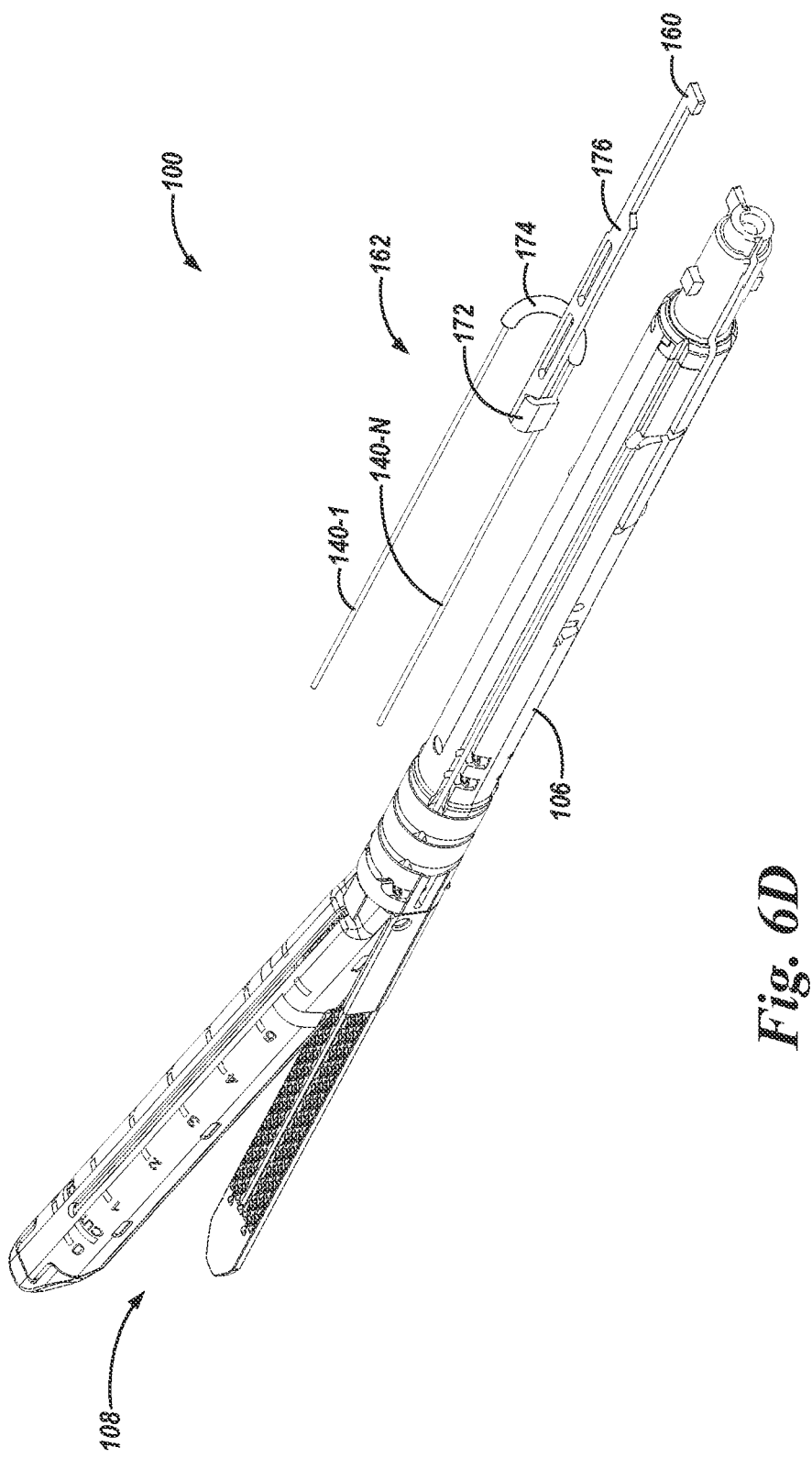
FIG. 6D is an exploded view of a mechanism for advancing and/or retracting pull wires in a multidirectional apparatus in accordance with a number of embodiments of the present disclosure.

FIG. 6D is an exploded view of a mechanism 162 for advancing and/or retracting pull wires 140-1, . . . , 140-N in a multidirectional apparatus 100 in accordance with a number of embodiments of the present disclosure. In this embodiment, two pull wires 140-1 and 140-N may be joined at their proximal end to form a single generally U-shaped wire. In some examples, 140-1 can be a first portion and 140-N can be a second portion of the same wire and a part of the first portion 140-1 and/or a part of the second portion 140-N can be located in the tube 174. Tab 160-2 is connected to bar 176 which is connected to pull wire 140-N by distal connector 172. Tube 174 is positioned within the shaft 106 of multidirectional apparatus 100 to provide a path for wire 140-1/140-N to move.

When tab 160 is moved in a distal direction, bar 176 and pull wire 140-N will also move in a distal direction. At the same time, pull wire 140-1 will move in a proximal direction causing jaw mechanism 108 to move away from the longitudinal axis of the multidirectional apparatus 100 in the direction of the proximally moving wire 140-1. In this embodiment, pull wire 140-N is shown as attached to bar 176 by distal connector 172. One or more of the number of pull wires 140-1, . . . , 140-N can be connected to the distal connector 172. In other embodiments, the connection between one or more of the number of pull wires 140-1, . . . , 140-N and bar 176 can be made through welding, brazing, or the like.

In some of the embodiments shown herein which comprise four pull wires 140-1, . . . , 140-N, the opposing pairs of pull wires 140-1 and 140-N can be located 45° from the opening/closing orientation of the jaw mechanism 108. In other embodiments, one set of opposing pairs of pull wires 140-1 and 140-N will line up with the opening/closing orientation of jaw mechanism 108 and the other opposing set of pull wires 140-2 and 140-3 will be 90° away. However, other angles are within the scope of this invention as well.

Figure 7:
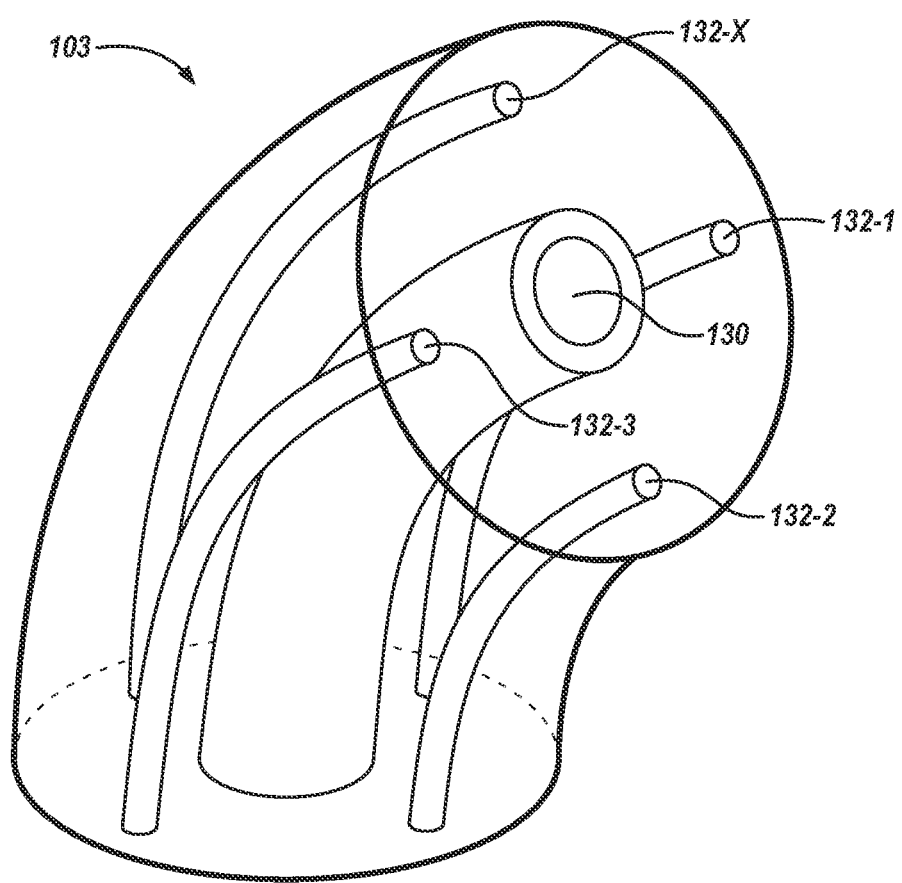
FIG. 7 is a transparent view of a composite articulation joint in accordance with a number of embodiments of the present disclosure.

FIG. 7 is a transparent view of a composite articulation joint 103. In this embodiment, joint 103 is a one-piece polymeric multi-lumen construction. In this transparent view, pull wire lumens 132-1, 132-2, 132-3, 132-X and central lumen 130 are shown. When assembled, each pull wire 140-1, . . . , 140-N will be positioned within a pull wire lumen 132-1, . . . , 132-X and sheath 112 will be positioned within lumen 130.

Instead of polymer or plastic, this embodiment of the articulation joint 103 can also be a composite structure. For example, pull wire lumens 132-1, . . . , 132-X may be lined with PTFE to minimize friction between the lumens 132-1, . . . , 132-X and the pull wires 140-1, . . . , 140-N. In some examples, lumen 130 can be provided with an integrated coil spring for extra strength and support.

Figure 8:
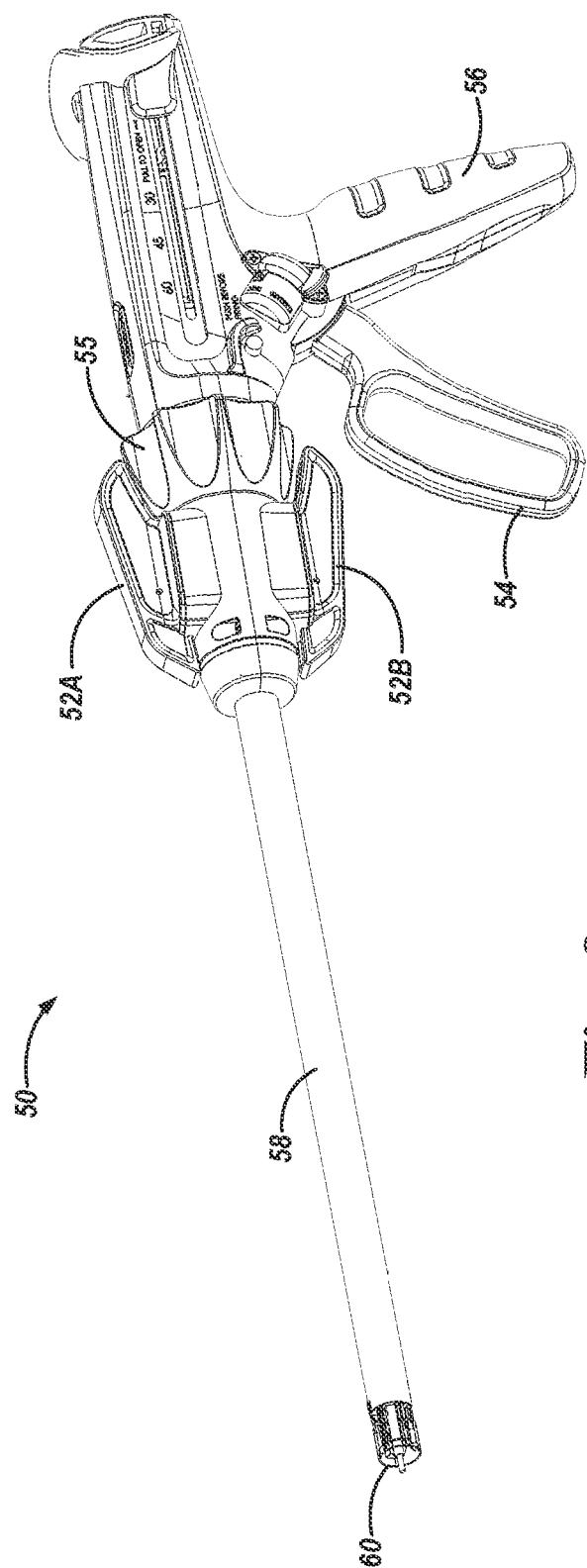
FIG. 8 is a perspective view of a surgical handle assembly in accordance with a number of embodiments of the present disclosure.

FIG. 8 is a perspective view of a surgical handle assembly 50 in accordance with a number of embodiments of the present disclosure. The surgical handle assembly 50 can be used with multidirectional apparatus 100 described herein.

Handle assembly 50 includes stationary handle 56 and moveable handle 54. Movement of moveable handle 54 causes a drive mechanism, not shown, to move within handle tube 58. When attached to multidirectional apparatus 100, a user can move moveable handle 54 toward handle 56 to move the drive mechanism in a distal direction causing first and second elongated members 107 and 109 to close. Further movement of the moveable handle 54 and the drive mechanism will cause thrust wire 110 to move distally causing I-beam 116 and stapling wedge 119 to move distally to deliver staples. Also shown are articulation levers 52A and 52B. When actuated, the articulation levers 52A and 52B cause independent articulation bars (e.g., articulation bars 68A and 68B in FIG. 9) to move proximally and distally. The independent articulation bars can actuate tabs 160-1 and 160-2, shown in FIG. 6A, causing the distal end of multidirectional apparatus 100 to articulate.

At the distal end of handle tube 58 is handle tube connection assembly 60 which connects with connector 111, shown in FIG. 1A. When the user rotates lever 52A, the jaw mechanism 108 will move in one plane. When the user rotates lever 52B, the jaw mechanism 108 will move in another plane. When both levers 52A and 52B are rotated, the user can achieve articulation of jaw mechanism 108 in any plane.

FIG. 8 also shows rotation knob 55. This feature allows the user to rotate the distal end of the handle assembly 50 and the multidirectional apparatus 100. Levers 52A and/or 52B allow articulation of the jaw mechanism 108 without rotation of the multidirectional apparatus 100.

FIG. 9 is an exploded view of a surgical handle assembly 50 in accordance with a number of embodiments of the present disclosure. In the embodiment shown in FIG. 9, there are two articulation mechanisms shown, A and B. While the following disclosure will be described relative to mechanism A, if the two mechanisms are identical, the description will equally apply to B. Articulation lever 52A is mounted on nose piece 62A and connected to rotating cam 64A. When the user rotates articulation lever 52A, rotating cam 64A also rotates. Rotating cam 64A interfaces with slotted bracket 66A and, when rotating cam 64A is rotated, slotted bracket 66A will move in either a distal or proximal direction. Slotted bracket 66A is connected to articulation bar 68A. When articulation lever 52A is rotated, rotating cam 64A rotates, which causes slotted bracket 66A to move either proximally or distally and articulation bar 68A will also move proximally or distally, respectively. At the distal end of articulation bar 68A, is cut out 70A. When connected to multidirectional apparatus 100, cut out 70A interfaces with one of tabs 160-1 and 160-2, shown in FIG. 6A, and cut out 70B interfaces with the other one of tabs 160-1 or 160-2. The articulation mechanism as shown in FIG. 9 is also described in U.S. application Ser. No. 16/027,579, entitled Surgical Handle Articulation Assembly, filed Jul. 5, 2018, which is incorporated herein by reference. While rotation mechanisms A and B are shown as being identical, they do not have to be. Other articulation mechanisms can also be used with the inventions described herein.

In some embodiments, articulation bars 68A and 68B will be controlled by one or two electric motors. In this embodiment, the surgical handle assembly 50 may comprise a joystick or other mechanism in electronic communication with the motor(s) to allow the user to control the articulation. In other embodiments, a touch sensitive directional pad may be used to control the articulation. In other embodiments, the handle assembly 50 may comprise two rocker or other type of switches, one for each articulation bar 68A and 68B, that will activate the electric motor(s) to control the articulation.

In some embodiments, the reload device 100 and handle assembly 50 may be provided to a user, such as a physician, individually. To use, the user will attach the multidirectional apparatus 100 to the surgical handle assembly 50. When used in minimally invasive surgery, the distal end of the connected multidirectional apparatus 100 and the surgical handle assembly 50 will be inserted through a trocar or a similar device to allow the user to position the distal end of the multidirectional apparatus 100 and the surgical handle assembly 50 at the desired location.

To assist in positioning the multidirectional apparatus 100 and the surgical handle assembly 50 at the proper location, the user may rotate one or both of the articulation levers 52A and 52B. Moving only one of the articulation levers 52A and 52B will cause the jaw mechanism 108 to move in one plane. By actuating both articulation levers 52A and 52B, the user can cause the jaw mechanism 108 to move in any direction without rotating the jaw mechanism 108.

Once positioned, the user will move the moveable handle 54 toward the stationary handle 56 to cause the distal elongated members 107 and 109 to close around the tissue to be stapled. Further strokes of the moveable handle 54 will cause the staples located in one of the elongated members 107 and 109 to be delivered as the I-beam 116 is moved in a distal direction. The movement of the I-beam 116 also cuts the tissue located between the rows of staples. When the staples are delivered, the user removes the multidirectional apparatus 100 and the surgical handle assembly 50 from the patient. If more staples are required, the used multidirectional apparatus 100 may be disconnected from the surgical handle assembly 50 and a new multidirectional apparatus 100 may be attached or a staple cartridge can be disconnected from the multidirectional apparatus 100 and a new staple cartridge may be attached.

In a number of embodiments herein, the surgical handle assembly 50 is shown as being manually actuated. Other handle assemblies such as ones that are driven by an electric motor may also be used. In these motor driven handle assemblies 50, a disposable or reusable/rechargeable battery may be used. It is also envisioned that the surgical handle assembly 50 could be replaced by a robotic or remotely controlled mechanism. In this embodiment, the physician/user is remote from the patient and controls the device from a computer input station or the like. In this embodiment, the multidirectional apparatus 100 would be connected to a robotic or remotely controlled arm.

In some examples herein, the multidirectional apparatus 100 is shown to include a connection to the surgical handle assembly 50, a shaft 106, and the jaw mechanism 108. The inventions described herein are equally applicable to a configuration wherein the surgical handle assembly 50 comprises the handle and the articulation mechanism. In this embodiment, the entire articulation mechanism will be in the handle tube 58 of the surgical handle assembly 50 and the surgical handle assembly 50 can be coupled to a reload assembly. The reload assembly could comprise a connector and the jaw mechanism 108 or just a staple cartridge. In the connector and jaw mechanism 108 embodiment, the reload assembly will include all components distal of connector 104 and the surgical handle assembly 50 will include the handle drive mechanism with the last section of the drive mechanism being constructed similar to thrust wire 110. In the staple cartridge embodiment, the I-beam 116 will be part of surgical handle assembly 50 and will be reused for each reloadable cartridge and the staple cartridge will include the hypo tube 118 as described herein.

FIG. 10A is a side view of multidirectional apparatus 100 in accordance with a number of embodiments of the present disclosure. In a number of embodiments, at least two springs of the number of springs 80-1, 80-2, 80-3, . . . , 80-M are on either side of at least one wire guide plate of the number of wire guide plates 81-1, 81-2, 81-3, 81-4, . . . , 81-P. The number of wire guide plates 81-1, . . . , 81-P can each have a short cylindrical shape with a lumen in the center for sheath 112 and/or thrust wire 110 and a lumen for each pull wire 140-1, . . . , 140-N. The articulation joint 103 can comprise alternating springs 80-1, . . . , 80-M and wire guide plates 81-1, . . . , 81-P.

Figure 10B:
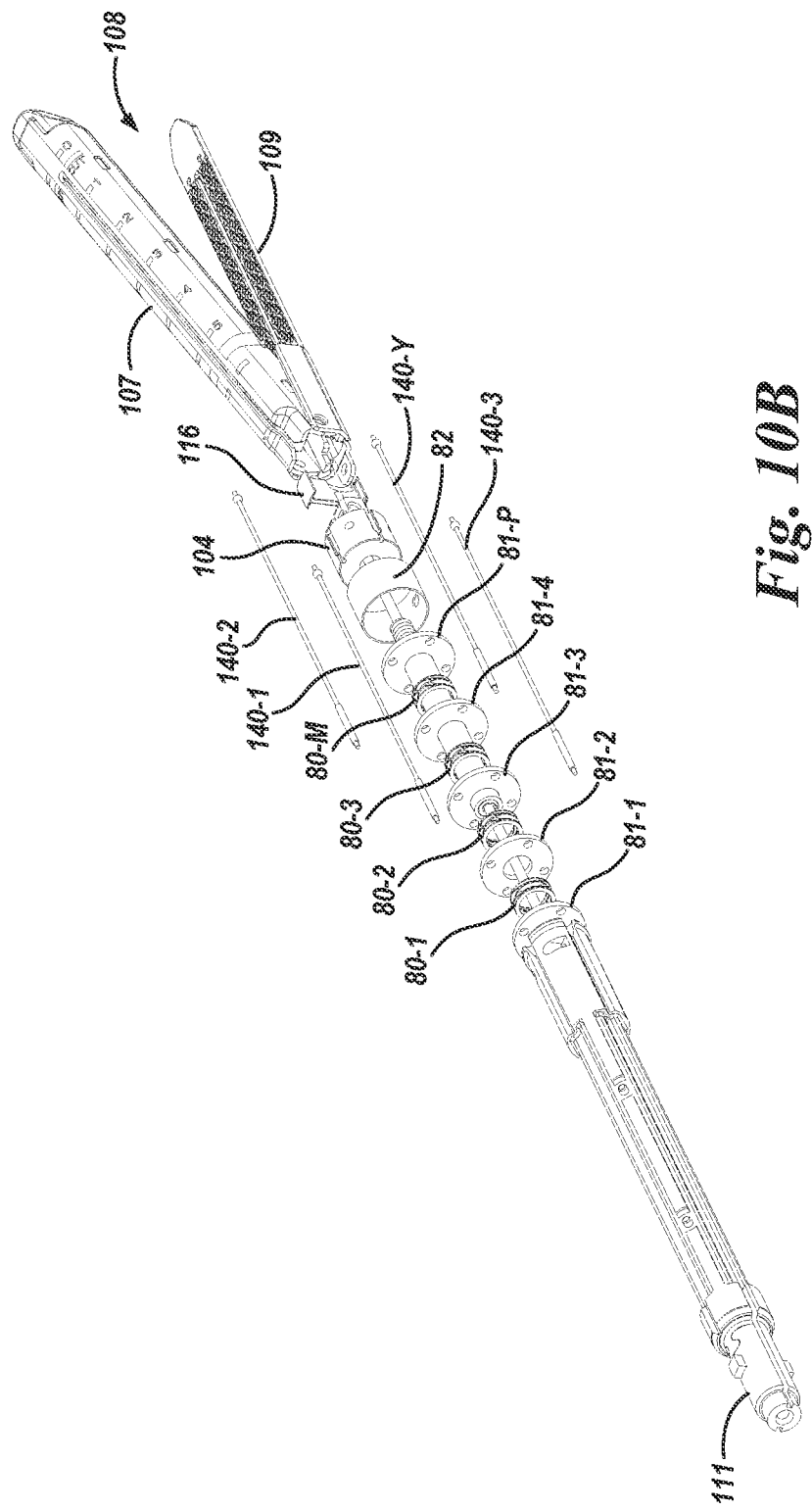
FIG. 10B is an exploded view of a multidirectional apparatus in accordance with a number of embodiments of the present disclosure.

FIG. 10B is an exploded view of multidirectional apparatus 100 in accordance with a number of embodiments of the present disclosure. In the exploded view of FIG. 10B, the number of pull wires 140-1, . . . , 140-Y are connected at their distal end to connector 104. The multidirectional apparatus 100 can include a containment tube 82 that can be positioned over connector 104.

The embodiment shown in FIG. 10B comprises five wire guide plates 81-1, 81-2, 81-3, 81-4, . . . , 81-P and four springs 80-1, 80-2, 80-3, . . . , 80-M. In some embodiments, articulation joint 103 will comprise a single wire guide plate 81-2 surrounded by two spring elements 80-1 and 80-2. As shown in FIG. 10B, springs 80-1, . . . , 80-M can be stacked wave disc springs. Alternatively, springs 80-1, . . . , 80-M can be helical springs or other similar devices. When constructed, in some embodiments, the springs 80-1, . . . , 80-M can be under slight compression. Maintaining the springs 80-1, . . . , 80-M under slight compression can keep the distal jaw mechanism 108 lined up with the longitudinal axis of the multidirectional apparatus 100 and can keep even spacing between the wire guide plates 81-1, . . . , 81-P. Other aspects of the device shown in FIG. 10A are as described herein with respect to other embodiments.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A surgical device, comprising:
    a surgical handle assembly comprising a first articulation lever and a second articulation lever, wherein movement of the first articulation lever results in axial movement of a first articulation bar, and wherein movement of the second articulation lever results in axial movement of a second articulation bar; and
    a multidirectional apparatus, comprising:
        an articulation joint configured to articulate 360° around a longitudinal axis of the multidirectional apparatus,
        a first pair of pull wires,
        a second pair of pull wires,
        a first mechanism for moving the first pair of pull wires, and
        a second mechanism for moving the second pair of pull wires,
    wherein movement of the first articulation lever results in movement of the first articulation bar that, in turn, actuates the first pair of pull wires to move a distal end of the multidirectional apparatus relative to the longitudinal axis of the multidirectional apparatus.

2. The surgical device of claim 1, wherein movement of the first articulation lever in a first direction results in distal movement of the first articulation bar that, in turn, actuates a first pull wire of the first pair of pull wires to move distally and a second pull wire of the first pair of pull wires to move proximally.

3. The surgical device of claim 2, wherein movement of the first articulation lever in a second direction results in proximal movement of the first articulation bar that, in turn, actuates the first pull wire of the first pair of pull wires to move proximally and the second pull wire of the first pair of pull wires to move distally.

4. The surgical device of claim 1, wherein movement of the second articulation lever results in movement of the second articulation bar that, in turn, actuates the second pair of pull wires to move the distal end of the multidirectional apparatus relative to the longitudinal axis of the multidirectional apparatus.

5. The surgical device of claim 4, wherein movement of the second articulation lever in a first direction results in distal movement of the second articulation bar that, in turn, actuates a first pull wire of the second pair of pull wires to move distally and a second pull wire of the second pair of pull wires to move proximally.

6. The surgical device of claim 5, wherein movement of the second articulation lever in a second direction results in proximal movement of the second articulation bar that, in turn, actuates the first pull wire of the second pair of pull wires to move proximally and the second pull wire of the second pair of pull wires to move distally.

7. The surgical device of claim 1, wherein a first tab is coupled to a distal end of the first articulation bar, and wherein a second tab is coupled to a distal end the second articulation bar.

8. A surgical device, comprising:
a surgical handle assembly comprising a first articulation lever and a second articulation lever, wherein movement of the first articulation lever results in axial movement of a first articulation bar; and
a multidirectional apparatus, comprising:
an articulation joint configured to articulate 360° around a longitudinal axis of the multidirectional apparatus,
a first pull wire,
a second pull wire, and
a mechanism for moving the first and second pull wires,
wherein movement of the first articulation lever results in movement of the first articulation bar that, in turn, actuates the first and second pull wires to move a distal end of the multidirectional apparatus relative to the longitudinal axis of the multidirectional apparatus.

9. The surgical device of claim 8, wherein movement of the first articulation lever in a first direction results in distal movement of the first articulation bar that, in turn, actuates the first pull wire to move distally and the second pull wire to move proximally.

10. The surgical device of claim 9, wherein movement of the first articulation lever in the first direction results in movement of the distal end of the multidirectional apparatus in a second direction away from the longitudinal axis of the multidirectional apparatus.

11. The surgical device of claim 9, wherein movement of the first articulation lever in a second direction results in proximal movement of the first articulation bar that, in turn, actuates the first pull wire to move proximally and the second pull wire to move distally.

12. The surgical device of claim 11, wherein movement of the first articulation lever in the second direction results in movement of the distal end of the multidirectional apparatus in a third direction away from the longitudinal axis of the multidirectional apparatus.

13. The surgical device of claim 8, wherein the mechanism for moving the first and second pull wires includes a pinion that mates with a rack to cause the second pull wire to move proximally in response to distal movement of a first tab.

14. The surgical device of claim 8, wherein the mechanism for moving the first and second pull wires includes a pinion that mates with a rack to cause the second pull wire to move distally in response to proximal movement of a first tab.

15. A surgical device, comprising:
a shaft with a proximal end, a distal end, and a longitudinal axis;
an articulation joint positioned at the distal end of the shaft, the articulation joint comprising at least two articulation elements;
at least two pull wires positioned within each of the at least two articulation elements, wherein the at least two pull wires are connected to the articulation joint; and
a jaw mechanism positioned distal of the at least two articulation elements, wherein tension applied to a first pull wire of the at least two pull wires will cause the jaw mechanism to move away from the longitudinal axis of the shaft and towards the first pull wire.

16. The surgical device of claim 15, wherein tension applied to a second pull wire of the at least two pull wires will cause the jaw mechanism to move away from the longitudinal axis of the shaft and towards the second pull wire.

17. The surgical device of claim 15, wherein distal movement of a mechanism for moving the at least two pull wires actuates the first pull wire of the at least two pull wires to move distally and actuates a second pull wire of the at least two pull wires to move proximally.

18. The surgical device of claim 17, wherein proximal movement of the mechanism for moving the at least two pull wires actuates the first pull wire of the at least two pull wires to move proximally and actuates the second pull wire of the at least two pull wires to move distally.

19. The surgical device of claim 17, wherein distal movement of the mechanism for moving the at least two pull wires causes the jaw mechanism to move away from the longitudinal axis of the shaft and towards the second pull wire.

20. The surgical device of claim 17, wherein proximal movement of the mechanism for moving the at least two pull wires causes the jaw mechanism to move away from the longitudinal axis of the shaft and towards the first pull wire.

* * * * *